United States Patent [19]

Drews

[11] 4,119,096
[45] Oct. 10, 1978

[54] MEDICAL INHALATION DEVICE FOR THE TREATMENT OF DISEASES OF THE RESPIRATORY TRACT

[75] Inventor: Wolf-Dietrich Drews, Munich, Germany

[73] Assignee: Siemens Aktiengesellschaft, Berlin & Munich, Germany

[21] Appl. No.: 717,343

[22] Filed: Aug. 24, 1976

[30] Foreign Application Priority Data

Aug. 25, 1975 [DE] Fed. Rep. of Germany ....... 2537765

[51] Int. Cl.² .......................................... A61M 11/00
[52] U.S. Cl. .................... 128/194; 128/198; 128/DIG. 2; 261/DIG. 65; 261/DIG. 48; 239/102
[58] Field of Search ............... 128/198, 195, 194, 193, 128/201, DIG. 2, 188, 173 R, 172 R; 259/DIG. 44; 261/DIG. 48, DIG. 65; 239/102; 200/61.52

[56] References Cited

U.S. PATENT DOCUMENTS

| 2,949,900 | 8/1960 | Bodine | 239/102 |
|---|---|---|---|
| 3,067,948 | 12/1962 | Lang et al. | 259/DIG. 44 |
| 3,469,785 | 9/1969 | Boucher et al. | 239/102 |
| 3,599,745 | 8/1971 | Hughes | 200/61.52 |
| 3,637,981 | 1/1972 | Swimmer | 200/61.52 |
| 3,682,167 | 8/1972 | Urbanowica | 128/194 |
| 3,812,853 | 5/1974 | Crain | 128/173 R |
| 3,812,854 | 5/1974 | Michaels et al. | 128/DIG. 2 |

FOREIGN PATENT DOCUMENTS 2,239,950 3/1974 Fed. Rep. of Germany.
1,035,049 7/1966 United Kingdom ..................... 128/194

Primary Examiner—Henry J. Recla
Attorney, Agent, or Firm—Hill, Gross, Simpson, Van Santen, Steadman, Chiara & Simpson

[57] ABSTRACT

An inhalator is constructed with an outer housing and an inner protective housing. The outer housing includes an opening adapted to receive the anatomy of the nasal region. The outer housing also contains a reservoir for holding a supply of medicinal liquid. The inner housing contains and protects an oscillator which energizes an electromechanical transducer, the transducer extending through a wall of the protective housing in sealed relation thereto and carrying a vibratory atomizing member which is positioned to receive liquid from the reservoir. The oscillator includes a position sensitive on-off switch which permits operation only when the inhalator is in a predetermined orientation. A droplet shield is positioned forward of the atomizing member, between the atomizing member and the opening in the outer housing so that liquid droplets of the aerosol and respiration moisture precipitate thereon and run off along a path over which the droplets will not strike the atomizing member.

2 Claims, 2 Drawing Figures

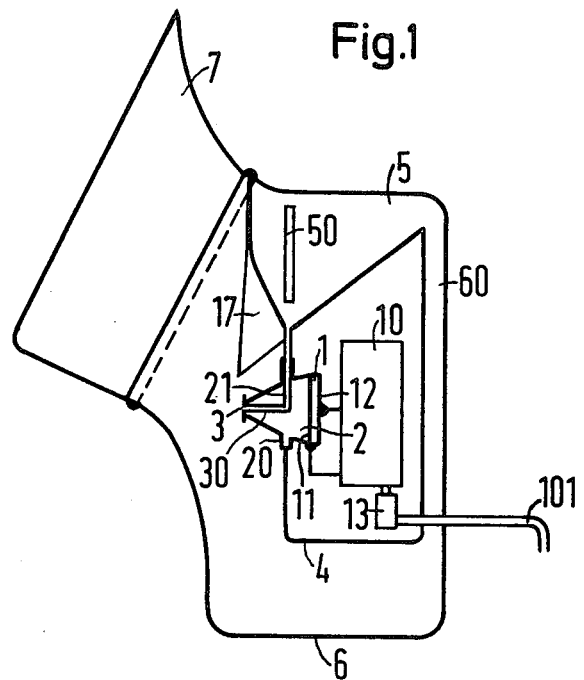
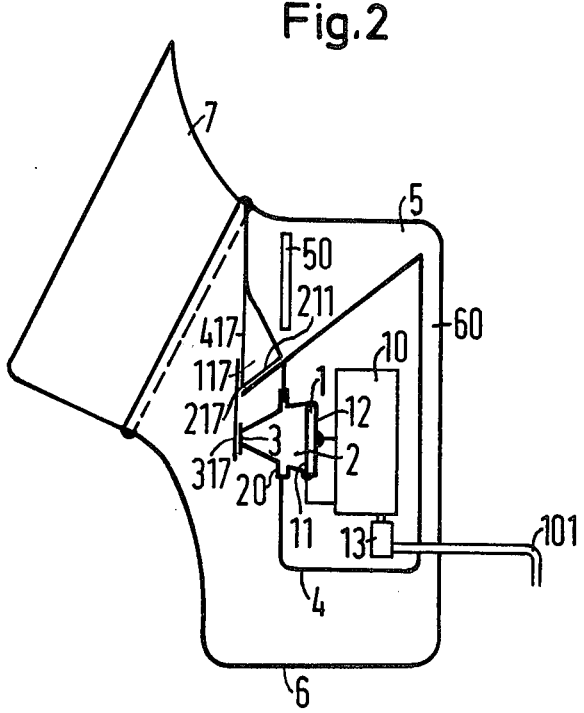

MEDICAL INHALATION DEVICE FOR THE TREATMENT OF DISEASES OF THE RESPIRATORY TRACT

BACKGROUND OF THE INVENTION

1. Field of the Invention

The present invention relates to an ultrasonic liquid atomizer, and more particularly to an ultrasonic liquid atomizer for inhalation therapy.

2. Description of the Prior Art

Medicinal aerosols have heretofore been produced with devices which have a very expensive construction. Because of their weight and because they must be connected to an electrical outlet, these commercially common atomizing devices are very bulky and unwieldly for patient use.

SUMMARY OF THE INVENTION

It is therefore the primary object of the invention to provide a hand device which is extraordinarily strong, light-weight and handy, and which permits operation independently of an electrical outlet.

This object is achieved in an ultrasonic liquid atomizer which includes an outer housing having an opening adapted to receive the anatomy of the nasal region and including therein a liquid reservoir for holding a supply of medicinal liquid, and an ultrasonic electromechanical transducer having an atomizer plate in fluid communication with the reservoir. Preferably, the oscillatory system includes an excitation circuit which is connected to a piezoceramic layer carried on a conically-shaped sonic transducer which transmits ultrasonic flexural waves onto an atomizer plate carried by the transducer. The conically-shaped sonic transducer is provided with a retaining ring at a node thereof and the retaining ring mounts the transducer in somewhat of a cantilever fashion in a wall of a protective housing within the outer housing, the protective housing containing the piezoceramic layer and the excitation circuit. In one embodiment the reservoir is connected in fluid communication with the atomizing plate by way of a fluid passageway which extends through the transducer in the plane of the retaining ring and then axially through the transducer and the atomizing plate. In another embodiment, the reservoir is provided with a fluid passageway which extends toward the outer surface of the atomizing plate. In this embodiment, a mesh material functioning as a wick with a capillary-type action, may be provided to extend from the fluid passageway over the outer face of the atomizing plate.

BRIEF DESCRIPTION OF THE DRAWINGS

Other objects, features and advantages of the invention, its organization, construction and operation will be best understood from the following detailed description, taken in conjunction with the accompanying drawings, on which:

FIG. 1 is a schematic illustration of an embodiment of an inhalator constructed in accordance with the invention; and FIG. 2 is a schematic illustration of another embodiment of an inhalator constructed in accordance with the invention and utilizing capillary action for feeding a medicinal liquid to an atomizing plate.

DESCRIPTION OF THE PREFERRED EMBODIMENTS

The atomizer of the present invention advantageously employs a piezoelectric oscillatory system, such as the system described in the German DOS No. 2,308,584 and in U.S. Pat. No. 3,904,896. Referring to FIG. 1, in the oscillatory system, flexural waves are generated by means of a piezoceramic layer 1 and are transmitted by a conically-shaped transducer 2 to an atomizer plate 3. In the region of an oscillation node, the transducer is provided with a retaining ring 20 which mounts the transducer in a freely-supported manner, in the wall of a liquid-proof protective housing 4 so that the piezoceramic layer is shielded from the liquid to be atomized. Additionally, an electronic excitation circuit 10 is mounted in the protective housing 4. The electronic excitation circuit applies an alternating voltage to the piezoceramic layer by way of an electrode 11 and an electrode 12. The electronic excitation circuit is supplied with a dc voltage, for example between 6 and 12 volts by way of a feed line 101 which extends through a wall of the outer housing 6 and a wall of the protective housing 4 in a liquid-type manner. The feed line 101 may be connected to a battery or to an outlet plug having a built-in rectifier. In case of operation from an electrical outlet, a higher dc voltage, for example 24 volts, is preferred.

The atomizer plate 3 is supplied with liquid by way of a bore 30 which extends along the longitudinal axis of the sonic transducer, and via a further bore 21 which extends in the plane of the retaining ring 20. The liquid is held in a container (reservoir) 5 which is preferably a funnel-shaped structure, the liquid being transported to the atomizer plate 3 by gravity. The liquid container 5 is, together with the oscillatory system, built into an atomizer housing 6. The housing 6 has an opening in the vicinity of the atomizer plate 3, and an attachment 7 can be emplaced, such as with a snap-on fit, which attachment is fitted to the anatomy of the nasal region. When the atomizer is operated, fine mist droplets are produced by the atomizer plate and only the finest droplets remain suspended and reach the attachment 7 for inhalation by a patient. The larger droplets fall down into the housing 6 and are caught by the bottom wall of the housing. Advantageously, therefore, under the influence of gravity, the droplet size of the aerosol is homogenized. The liquid caught at the bottom of the housing can be transported, via a return conduit 60, back into the liquid container 5 by simply tipping the device.

When the device is not in use, the outlet opening can be closed with a cover, which is emplaced instead of the attachment 7, again advantageously by a snap-on engagement.

Preferably, a position dependent switch 13 is built into the protective housing, for example a mercury switch, so that the device automatically turns itself on when it is held in a working position, i.e., with the liquid container 5 located at the top, as illustrated on the drawings. In any other position, the electrical connection of the electronic exciter circuit to the current supply remains interrupted.

At a side of the housing, in the region of the liquid container 5, a viewing window 50 may be provided so that the liquid level can be ascertained at any time.

In order to avoid having liquid drops blown against the transducer 2 when the patient exhales, a drop shield 17 can be provided, which shield is arranged above the transducer, or, respectively, the atomizer plate 3, in the direction toward the housing opening, in such a way that liquid drops of the aerosol and of the respiration moisture precipitate and run off on the front side 171 facing the housing opening. The front side 171 extends in a vertical direction, looking toward the housing opening, above and forward of the position of the atomizer plate in such a way that the drops running off no longer reach the oscillatory system, in particular onto the surface of the atomizer plate 3.

In order to refill the device, the medicinal liquid is simply poured into the housing 6, and the device is tipped so that the liquid flows to the reservoir container 5 by way of the conduit 60.

It has been determined that particularly finely-particled aerosols can be obtained with an inhalator constructed in accordance with the invention if the excitation of the oscillatory system, i.e., the electric power supplied to the oscillatory system, is dimensioned in such a way that the operation of the oscillatory system or, respectively, the atomization, has a working point which is only slightly above the initiation threshold. The term "initiation threshold" is to be understood to mean the beginning of the oscillatory state of the oscillatory system or, respectively, of the atomizing plate. With the selection of this working point, it is advantageously achieved that the size distribution of the droplets is very homogeneous, even at low oscillatory frequencies. With an inhalation device constructed in accordance with the present invention, advantageous operation is possible at oscillatory frequencies of 200 to 500 kHz. According to previous findings, it was necessary to operate with frequencies in the range of MHz for relatively small droplets in the order of magnitude of between 1 to 6 μm diameter, which requires considerable expense for the electronics and also results in a lesser efficiency.

Referring to FIG. 2 now another embodiment of the invention is illustrated which is similar to that illustrated in FIG. 1 but which deviates therefrom in that the liquid supply onto the surface of the atomizer plate 3 takes place through a passageway 211 and via a network structure 317 which will be described in greater detail below, instead of by way of the passageway 21, 30. The passageway 211 is located in a part 117 and extends, starting at the liquid container 5, in a downward direction to an outlet opening 217 which is situated above and spaced from the atomizer plate 3, the liquid from the container 5 reaching the opening 217 by means of gravity in all operating positions of the inhalation device.

Above and beyond the outlet opening 217 and the top of the atomizer plate 3, the above-mentioned network structure 317 is attached to the front side 417 of the part 117, if necessary in an easily exchangeable fashion. Preferably, the front side 417 and the surface of the atomizer plate 3 lie in the same plane so that the network structure 317 rests smoothly, in suspension, on the surfaces.

The function of the network structure 317 is to transport the liquid from the outlet opening 217 to the surface of the atomizer plate 3 with a wick or capillary action. The dosage of the liquid supply occurs, on the one hand, as a result of the selection of the cross section of the passageway 211 and, on the other hand, by means of the wick or capillary action of the network structure 317.

Felted or matted cellulose fibers, such as for example a finely woven network, as from Kleenex tissues, made of synthetic materials such as Perlon (a synthetic material similar to nylon) having mesh apertures of, for example, 100 μm and less, and the like are suitable as network structures for an inhalator constructed in accordance with the principles illustrated in FIG. 2. Advantageously, the network structure 317 is not permitted to protrude substantially beyond the lower edge of the atomizer plate 3.

If necessary, a valve (not shown) is provided in all embodiments of the invention, in the region of the passageway 21 or the passageway 211, with which the liquid flow out of the container 5 is blocked when the device is taken out of operation.

It can also be provided that the liquid container 5 be removable from the device or, respectively, interchangeable liquid containers may be provided.

Although I have described my invention by reference to particular illustrative embodiments thereof, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. A hand-held inhalator comprising:

an outer housing including means defining an opening shaped to receive the anatomy of the nasal regions;

wall means defining an inner protective chamber within said outer housing;

an oscillator mounted within said inner chamber, said oscillator including an electronic excitation and a piezoceramic member electrically connected to and excitable into vibration by said electronic excitation circuit, electrical supply leads connected to said electronic excitation circuit and extending in fluid-sealed relation through said chamber and outer housing for connection to an electrical supply, and switch means electrically connected in said electrical supply leads and operable to activate said electronic excitation circuit when said supply leads are connected to an electrical supply;

a conically-shaped sonic transducer extending through said wall means and mounted thereto in a liquid-tight relation at an oscillation node, said transducer carrying said piezoceramic member on its larger end, and including an atomizing plate mounted on the smaller end of said conically-shaped sonic transducer, said atomizing plate including a surface facing the opening in said outer housing, said transducer transmitting ultrasonic vibrations to said plate; and a liquid reservoir in said outer housing including an unobstructed outlet passageway means and wick means providing sole fluid communication from said outlet passageway means to said surface of said atomizing plate.

2. A hand-held inhalator comprising:

an outer housing including means defining an opening shaped to receive the anatomy of the nasal region;

wall means defining an inner protective chamber within said outer housing;

an oscillator mounted within said inner chamber, said oscillator including an electronic excitation circuit and a piezoceramic member which is connected to and excitable into vibration by said electronic excitation circuit;

a conically-shaped sonic transducer extending through said wall means and mounted thereto in a liquid-tight relation at an oscillation node, said transducer carrying said piezoceramic member on its larger end, and including an atomizing plate mounted on the smaller end of said conically shaped sonic transducer, said atomizing plate including a surface facing the opening in said outer housing, said transducer transmitting ultrasonic vibrations to said plate; and a liquid reservoir in said outer housing including an unobstructed outlet passageway means extending from said reservoir to a point adjacent said atomizing plate, and a mesh network constituting a wick extending in fluid communication between said outlet passageway means and said surface of said atomizing plate and providing sole fluid communication therebetween.

* * * * *